United States Patent [19]
Garcia Lopez et al.

[11] Patent Number: 6,146,871
[45] Date of Patent: Nov. 14, 2000

[54] PROCESS FOR MODIFYING THE ENZYME 7β-(4-CARBOXYBUTANAMIDE) CEPHALOSPORINACYLASE AND PURIFYING SAID ENZYME IN A SINGLE CHROMATOGRAPHIC STEP

[75] Inventors: Jose Luis Garcia Lopez; Estrella Cortes Rubio; Jose Manuel Guisan Seijas, all of Madrid; Jose Luis Barredo Fuente, Leon; Bruno Diez Garcia, Leon; Alfonso Collados de la Vieja, Leon; Alejandro Vitaller Alba, Leon; Francisco Salto Maldonado, Madrid, all of Spain

[73] Assignee: Sntibioticos, S. A., Madrid, Spain

[21] Appl. No.: 08/981,321

[22] PCT Filed: Apr. 18, 1997

[86] PCT No.: PCT/ES97/00098

§ 371 Date: Aug. 13, 1998

§ 102(e) Date: Aug. 13, 1998

[87] PCT Pub. No.: WO97/40175

PCT Pub. Date: Oct. 30, 1997

[30] Foreign Application Priority Data

Apr. 19, 1996 [ES] Spain ...................................... 9600890

[51] Int. Cl.[7] .............................. C12N 9/18; C12N 15/00; C12N 15/55; C12N 15/70

[52] U.S. Cl. ................... 435/227; 435/69.1; 435/252.33; 435/320.1; 435/471; 435/47; 435/228; 530/413; 536/23.2; 536/23.4

[58] Field of Search .............................. 435/69.1, 252.33, 435/227, 228, 320.1, 471, 42–51; 536/23.2

[56] References Cited

U.S. PATENT DOCUMENTS

| | | | |
|---|---|---|---|
| 4,569,794 | 2/1986 | Smith et al. ............................. | 260/113 |
| 5,284,933 | 2/1994 | Dobeli et al. ........................... | 530/350 |
| 5,618,717 | 4/1997 | Wei et al. ............................... | 435/325 |
| 5,648,244 | 7/1997 | Kuliopulos et al. .................... | 435/69.7 |
| 5,650,313 | 7/1997 | Ni et al. .................................. | 435/193 |
| 5,686,579 | 11/1997 | Shami et al. .......................... | 530/387.3 |
| 5,723,311 | 3/1998 | Wei et al. ............................... | 435/69.1 |
| 5,763,590 | 6/1998 | Peattie et al. .......................... | 536/23.5 |
| 5,786,193 | 7/1998 | Greene et al. .......................... | 435/193 |
| 5,845,043 | 12/1998 | Johnson ................................. | 435/194 |

FOREIGN PATENT DOCUMENTS

| | | |
|---|---|---|
| 469919 | 2/1992 | European Pat. Off. . |
| 9115589 | 10/1991 | WIPO . |

OTHER PUBLICATIONS

Lilius, G., et al., European Journal of Biochemistry, vol. 198, "Metal affinity precipitation of proteins carrying genetically attached polyhistidine affinity tails", pp. 499–504, 1991.

Howard, K. J., et al., Journal of Biological Chemistry, vol. 266, "Reconstitution and properties of homologous and chimeric HIV–1 .HIV–2 p66.p51 reverse transcriptase", pp. 23003–23009, 1991.

Krautwald, S., et al., Biochemical and Biophysical Research Communications, vol. 192, "Bacterially expressed murine CSF–1 possesses agonistic activity in its monomeric form", pp. 720–727, 1993.

(List continued on next page.)

*Primary Examiner*—Ponnathapu Achutamurthy
*Assistant Examiner*—William W. Moore
*Attorney, Agent, or Firm*—Ladas & Parry

[57] ABSTRACT

A procedure for producing a modified 7β-(4-carboxybutanamide) cephalosporinase enzyme which can be purified in a single chromatographic step. The procedure for production of the enzyme involves: mutagenizing the gene which codes for the enzyme from Acinetobacter sp. ATCC 53891 by inserting a nucleotide sequence coding for six histidine residues; fusing the mutant gene with high-efficiency promoter DNA sequences; transforming *Escherichia coli* cells with the fusion gene construct; growing the transformed *Escherichia coli* cells; and recovering the enzyme by the use of supports which contain metal chelates. 7-Aminocephalosporanic acid is an important intermediate for the manufacture of a wide range of antibacterial agents of the cephalosporin family.

18 Claims, 1 Drawing Sheet

OTHER PUBLICATIONS

Fukuoka, Y., et al., Immunology Letters, vol. 38, "Expression of biologically active C3a as fusion proteins", pp. 153–158, 1993.

Wu, D., et al., Journal of Neurochemistry, vol. 61, "Expression, purification, and characterization of recombinant *Drosophila choline* acetyltransferase", pp. 1416–1422, 1993.

Poon, R. Y., et al., Analytical Biochemistry, vol. 218, "Reversible immunoprecipitation using histidine—or glutathione S–transferase–tagged staphylococcal protein A", pp. 26–33, 1994.

Glickman, J. F., et al., Biochemical and Biophysical Research Communications, vol. 204, "Baculovirus–mediated high level expression of a mammalian DNA methyltransferase", pp. 1003–1008, 1994.

McIlhenny, R. A., et al., European Journal of Biochemistry, vol. 222, "Characterization of a polyhistidine–tagged form of human myristoyl–CoA: protein N–myristoyltranferase produced in *E. coli*", pp. 137–146, 1994.

Oswald, T., et al., Applied Micriobiology and Biotechnology, vol. 42, "Comparison of N–terminal affinity fusion domains: effect on expression level and product heterogeneity of recombinant restriction endonuclease EcoRV", pp. 73–77, 1994.

Kim, Y. G., et al., Proceedings of the National Academy of Sciences, U.S.A., vol. 91, "Chimeric restriction endonuclease, ultrabithorax homodomain linkage to FokI cleavage domain by enzyme engineering and expression in *E. coli*", pp. 883–887, 1994.

Mitchell, D. M., et al., FEBS Letters, vol. 368, "Rapid purification of wildtype and mutant cytochrome c oxidase from *Rhodobacter sphaeroides* by NI(2+)–NTA affinity chromatography", pp. 148–150, 1995.

Blum, E., et al., Gene, vol. 157, "PCR–directed preparation and single–step purification of highly active histidine–tagged restriction endonuclease HgiBI (GGWCC)", pp. 107–108, 1995.

Kakiuchi, N., et al., Biochemical and Biophysical Research Communications, vol. 210, "Bacterial expression and analysis of cleavage activity of HCV serine proteinase using recombinant and synthetic substrate", pp. 1059–1065, 1995.

Pekrun, K., et al., European Journal of Biochemistry, vol. 234, "Expression and characterization of the reverse transcriptase from type 1 human immunodeficiency virus using different baculoviral expression systems", pp. 811–181, 1995.

Li, S., et al., Journal of Biological Chemistry, vol. 271, "Expression and characterization of recombinant caveolin. Purification by polyhistidine tagging and cholerol–dependent incorporation into defined lipid membranes", pp. 568–573, 1996.

Ernst, S., et al., Biochemical Journal, vol. 315, "Expression in *E. coli*, purification and characterization of heparinase I from Flavobacterium heparinum", pp. 589–597, 1996.

Sunstrom, N. A., et al., Journal of Membrane Biology, vol. 150, "Ion channels formed by NB, an influenza B virus protein", pp. 127–132, 1996.

Aramori, Ichiro et al., "Cloning and Nucleotide Sequencing of a Novel 7B–(4–Carboxybutanamido) cephalosporanic Acid Acylase Gene of *Bacillus laterosporus* and its Expression in *Escheria coli* and *Bacillus subtilis*." Journal of Bacteriology, vol. 173, No. 24 (Dec. 1991), pp. 7848–7855.

Matsuda, Akio et al., "Cloning and Characterization of the Genes for Two Distinct Cephalosporin Acylases from a Pseudomonas Strain." Journal of Bacteriology, vol.69, No. 12, (Dec. 1987) pp. 5815–5820.

Ichikawa, Shigeaki et al., "Purification and Properties of 7B–(4–Carboxybutanamido)– cephalosporanic Acid Acylase Produced by Mutants Derived from Pseudomanas." Agric. Biol. Chem., vol. 45, No. 10 (Feb. 1981), pp. 2231–2236.

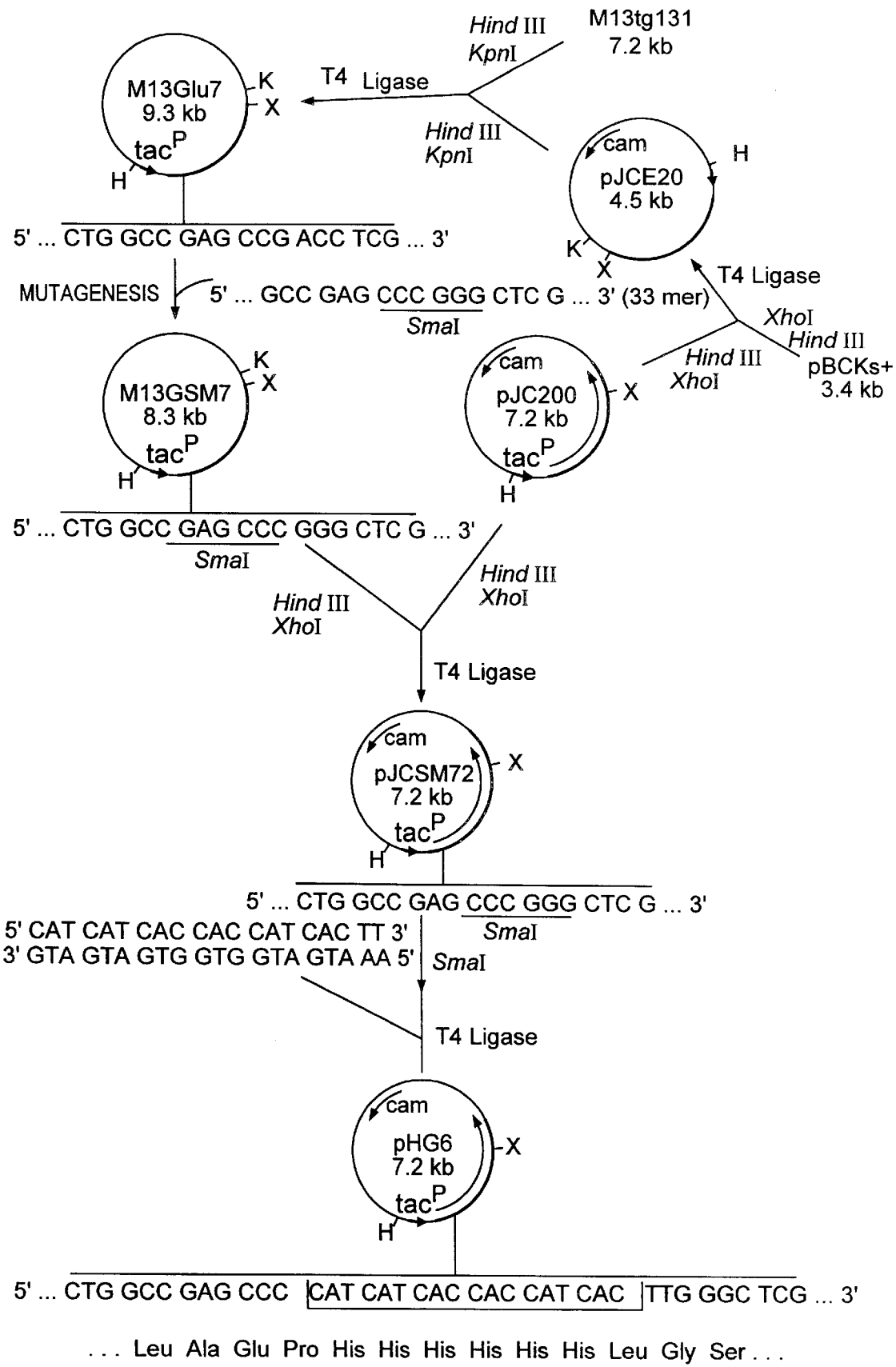

PROCESS FOR MODIFYING THE ENZYME 7β-(4-CARBOXYBUTANAMIDE) CEPHALOSPORINACYLASE AND PURIFYING SAID ENZYME IN A SINGLE CHROMATOGRAPHIC STEP

SCOPE OF THE INVENTION

The present invention relates to a procedure for modifying a gene which codes for an enzyme with 7β-(4-carboxybutanamide) cephalosporinacylase activity, by the use of recombinant DNA techniques. The modification made to the gene allows the purification of the said enzyme in a single chromatographic step. This modification consists in the fusion of a chain of six histidines to the aminoterminal end of the 7β-(4-carboxybutanamide) cephalosporinacylase, which allows it to bind with great affinity to adsorption chromatography columns with immobilized metallic ions.

This procedure would facilitate the enzymatic preparation of 7-aminocephalosporanic acid from 7β-(4-carboxybutanamide) cephalosporanic acid. 7-Aminocephalosporanic acid is a known intermediate for the manufacture of a wide range of antibacterial agents of the cephalosporin family.

STATE OF THE ART

For the production of 7β-(4-carboxybutanamide) cephalosporinacylase (hereinafter referred to as GLA) by fermentation, use has been made of micro-organisms such as Pseudomonas and Acinetobacter sp. The production of these enzymes by the said micro-organisms entails many disadvantages. Firstly, the GLA activity level is very low, and secondly, apart from the GLA activity, other enzymes are produced such as β-lactamases and acetylases which break down 7-aminocephalosporanic acid (hereinafter referred to as 7ACA), reducing the product yield and increasing the costs of the process for purification of the final product. In order to prevent this enzymatic contamination it is necessary to purify the GLA, which greatly increases the difficulties and costs of the enzymatic process for obtaining 7ACA acid from 7β-(4-carboxybutanamide) cephalosporanic acid (hereinafter referred to as GLA-7ACA).

Various procedures have recently been described for the isolation of genes which code for GLA (hereinafter referred to as gla gene) from strains such as Pseudomonas GK-16 (Matsuda et al. (1985) J. Bacteriol. 163, 1222–1228), Pseudomonas SE-83 (Matsuda et al. (1987) J. Bacteriol. 169, 5821–5826) and Acinetobacter sp. ATCC 53891 (Croux et al. (1990) Span. Pat. P9002109, Eur. Pat. 0469919A2, U.S. Pat. No. 5,354,667) and have been expressed in strains of *Escherichia coli*, commonly used in genetic engineering, extremely high levels of enzyme production being obtained, in comparison to those obtained in the parental strains.

In the process for purification of the enzymes expressed in *Escherichia coli*, co-purification of the unwanted enzymes referred to earlier (β-lactamases, esterases, etc.) is not entirely avoided, which means that the GLA obtained has to be purified in a number of chromatographic steps.

In the scientific literature no references have been found concerning any modification of the gla gene which would allow the enzyme GLA to be purified in a single chromatographic step.

GLA belongs to the group of beta-lactam acylases which, with the exception of penicillin V acylase, share a very similar molecular structure. These enzymes have a structure which is unusual among prokaryotic proteins; they are synthesized as an inactive precursor polypeptide which is secreted into the periplasmic space thanks to the presence of a signal peptide. This precursor is subsequently hydrolysed, releasing two polypeptides called the alpha subunit (16–25 kDa) and beta subunit (54–69 kDa); both join to form the active enzyme (Sudhakaran et al. (1992) Process Biochem. 27, 131–143). This type of processing common to all of them supports the idea that all of them belong to the same family of proteins and have evolved from a common ancestor.

With regard to substrate specificity, they can be divided into two groups. The first group comprises the beta-lactam acylases which are highly specific to penicillin G, but their specificity generally resides in the acyl residue of the substrate, which must be hydrophobic and preferably benzyl or alkyl. Examples of these enzymes are the penicillin G acylases of *Escherichia coli, Kluyvera citrophila, Proteus rettgeri, Alcaligenes faecalis, Arthrobacter viscosus* and *Bacillus megaterium* (Sudhakaran et al. (1992) Process Biochem. 27, 131–143).

The second group comprises the acylases which are able to hydrolyse cephalosporins with succinyl-, glutaryl- and adipyl-acyl residues, including cephalosporin C in some cases, although to a very limited extent (Sudhakaran et al. (1992) Process Biochem. 27, 131–143). These acylases known as GLAs have been found in Pseudomonas and Bacillus species (Sudhakaran et al. (1992) Process Biochem. 27, 131–143).

In general, in both cases the residue adjacent to the nitrogen atom of the amide group can be a cephem group, penem group, amino acid, etc.

BRIEF DESCRIPTION OF THE DRAWING

The FIGURE shows diagrammatically the genetic constructs used to clone a DNA fragment encoding six histidines into the gla gene of Acinetobacter sp. ATCC 53891.

DETAILED DESCRIPTION OF THE INVENTION

Using recombinant DNA techniques, the gla gene was modified in order to express an enzyme with a chain of six histidines in the region near to the terminal amino of the alpha subunit. The fusion of six histidines allows the enzyme to be purified in a single step in affinity chromatography columns with coordinated metallic ions.

In order to carry out the modification of the gla gene of Acinetobacter sp. ATCC 53891 (Croux et al. (1990) Span. Pat. P9002109, Eur. Pat. 0469919A2, U.S. Pat. No. 5,354, 667), this plasmid was digested with different restriction endonucleases in order to clone part of the gla gene in a vector which would allow a restriction target to be created, by site-directed mutagenesis, at a position adjacent to the nucleotide sequence coding for the N-terminal end of the alpha subunit of the enzyme. The fragment of the gla gene containing the mutation was subcloned again in the original vector, in order to reconstruct the complete gene. It was then cut with the restriction endonuclease, corresponding to the target created by site-directed mutagenesis, linearizing the plasmid, and was ligated with a double-stranded oligonucleotide coding for six histidines, by means of the enzyme T4 DNA ligase. The recombinant plasmids thus obtained were introduced by transformation into a strain of *Escherichia coli* auxotrophic for L-leucine, and the GLA-producing transformant clones were selected in a culture medium containing glutaryl-L-leucine as the sole source of L-leucine.

Competent cells were obtained with the aim of introducing the plasmids bearing the gla gene into *Escherichia coli* strains. Competent cells are cells which as a result of treatment, usually chemical, have altered membrane permeability and are able to accept exogenous DNA molecules. The said plasmids were introduced by transformation into the competent cells. Transformation is the procedure for introduction of exogenous DNA into the competent host cell.

In addition to the gla gene of Acinetobacter sp., the plasmids introduced had the chloramphenicol resistance gene as a selectable marker. In order to prove that the chloramphenicol-resistant *Escherichia coli* cells obtained by transformation carried the desired plasmids, minipreparations of plasmid DNA from a series of colonies isolated were made. The plasmids were subsequently analysed by conventional techniques.

In order to prove that the fusion had taken place correctly, the DNA coding for the N-terminal end of the alpha subunit of the modified enzyme was sequenced.

The production of modified GLA with a chain of polyhistidines was analysed using GL-7ACA as substrate and estimating the formation of 7ACA by a calorimetric technique.

In this way, a GLA-producing strain was obtained with a chain of six histidines in the N-terminal region of the alpha subunit, the production levels of which are similar to those of the type original clone. The strain obtained was deposited at the Spanish Culture Collection (CECT) Departmento de Microbiología, Facultad de Ciencias Biológicas Universidad de Valencia, 46100 Burjasot (Valencia), under the N° CECT 4637 on Feb. 7, 1996.

The second phase of the procedure consists in the purification of the modified GLA enzyme with a chain of six histidines in a single chromatographic step.

For this purpose, the recombinant *Escherichia coli* cells are grown in a previously selected medium containing a carbon source, a nitrogen source and mineral salts, for a period of 24–48 hours at a temperature of 30° C.

The GLA accumulated in the recombinant Escherichia coli cells can be recovered by centrifuging the culture medium in order to separate the cells, after which they are disrupted by conventional methods (pressure, sonication, etc.) and the extract obtained is purified by affinity chromatography with immobilized metallic ions.

In this type of chromatography the enzyme is retained in the column, whereas many of the proteins of the cell extract are eluted. Washing the chromatographic column with increasing concentrations of imidazole causes elution of the proteins of the extract which have been retained by weak interactions; the histidine-rich proteins remain bound to the column, the pure enzyme being obtained at high imidazole concentrations.

One of the innovations in this procedure is that it has been possible to modify the GLA enzyme in the N-terminal region of the alpha subunit without disturbing the complex process of maturation of the enzyme and without significantly changing its activity and enzymatic specificity. Another innovation is that the modification made to the enzyme appears to be located in an external zone of the molecule, as the histidines can interact with the metal chelates. This allows the enzyme to be obtained with a high degree of purity by means of a simple purification process, thus eliminating in a simple way the contamination from enzymes which are undesirable for the enzymatic preparation of 7ACA, as β-lactamases, esterases or catalases can be.

The present invention will be illustrated in greater detail in the examples which follow:

EXAMPLE 1

1. GLA Activity Assay

The enzymatic activity was assayed by the calorimetric method described earlier (Balasingham et al. (1972) Biochim. Biophys. Acta 276, 250–256).

2. Esterase Activity Assay

In order to demonstrate the presence of contaminating esterases, the ability of the sample to hydrolyse p-nitrophenylacetate (PNA) was measured. The tests were carried out in 0.8 ml of final reaction volume in Tris-HCl 0.1 M buffer (pH 7.5), using PNA as substrate (25 mM). The hydrolysis was monitored by recording the increase in absorbance at a wavelength of 400 nm.

3. Preparation of the DNA Vectors and Competent *Escherichia coli* Cells for Transformation The vector pBCKS (Stratagene) and the plasmid pJC200 (Croux et al. (1990) Span. Pat. P9002109, Eur. Pat. 0469919A2, U.S. Pat. No. 5,354,667) containing the gla gene of Acinetobacter sp. 53891 were prepared as follows: The *Escherichia coli* strains which individually had the aforesaid plasmids were incubated for 16 hours with shaking in an orbital shaker at 250 rpm and 37° C. in 0.5 liters of LB medium (containing 5 g/l of yeast extract, bactotryptone 10 g/l and 5 g/l of NaCl) and chloramphenicol (34 mg/l). After the time indicated had elapsed, the cells were sedimented, washed and lysed, and the plasmids were isolated by the alkaline method (Sambrook et al. (1989) Molecular Cloning: A laboratory manual, Cold Spring Harbor Laboratory, Cold Spring Harbor, N.Y., USA). The plasmid DNA obtained by this method was purified by centrifugation in CsCl gradient.

The phage M13tg131 (Amersham) was prepared as described earlier (Sambrook et al. (1989) Molecular Cloning: A laboratory manual, Cold Spring Harbor Laboratory, Cold Spring Harbor, N.Y., USA), using cells of *Escherichia coli* TG1 (Amersham) to prepare it.

The competent *Escherichia coli* cells were obtained by the RbCl procedure (Sambrook et al. (1989) Molecular Cloning: A laboratory manual, Cold Spring Harbor Laboratory, Cold Spring Harbor, N.Y., USA). Essentially the *Escherichia coli* strains TG1 (Amersham) and HB101 (Sambrook et al. (1989) Molecular Cloning: A laboratory manual, Cold Spring Harbor Laboratory, Cold Spring Harbor, N.Y., USA) were used for cloning and analysis of fragments.

4. Preparation of the AGAROSE-IDA-$Cu^{++}$ Support 2.4 g of $NaBH_3$ and 50 g of agarose Cl6B are added to a solution of 214 ml of 2M NaOH held at 4° C. This suspension is gently agitated while 122 ml of an acetone solution containing 41 ml of epichlorohydrin is slowly added to it. A further 41 ml of epichlorohydrin is added after 2 hours of agitation. A further 41 ml of pure epichlorohydrin is added after 2 hours of agitation. At 4 hours the reaction is stopped by washings with distilled water until the filtrate liquid has a pH of 7.0. In this way an agarose epoxide gel is obtained.

25 ml of 2 M sodium iminoacetate (IDA) is then prepared and mixed with 50 ml of 0.1 M carbonate-bicarbonate buffer, pH 11.0. 50 ml of agarose epoxide gel is added to this solution and the mixture is gently agitated at 25° C. for 18 hours. After the reaction has ended, the agarose-IDA gel formed is washed with copious distilled water until the filtrates have a pH of 7.0.

The agarose-IDA-$Cu^{++}$ gels were prepared by resuspending 50 ml of agarose-IDA gel in 200 ml of a 2% solution of pentahydrate copper sulphate. The suspension was gently agitated for 2 hours at 25° C. and washed with 500 ml of distilled water, followed by a washing with 500 ml of 0.2 M acid, containing 0.2 M NaCl and 0.0–1% Tween 20. Finally the gel was washed with 500 ml of distilled water.

EXAMPLE 2

1. Subcloning of a Fragment of the gla Gene in M13tg131 in Order to Create an SmaI Target by Site-Directed Mutagenesis In order to introduce a chain of six histidines into the N-terminal region of the alpha subunit of the GLA enzyme it was necessary first to create a target for a restriction endonuclease in the region of the DNA coding for the amino acids found in the bond between the signal peptide and the alpha subunit of the GLA. This would allow a nucleotide sequence coding for six histidines to be fused in this region.

The first step in the subcloning involved digesting the plasmid pJC200 with the endonucleases HindIII and XhoI and cloning it in pBCKS cut with the same restriction enzymes, as is shown in the drawing. This makes the KpnI and HindIII targets available for the subcloning of this fragment in the vector M13tg131 in which site-directed mutagenesis will be carried out using Ektein's method.

The plasmid pJC200 (2 μg) was treated with the restriction endonucleases HindIII and XhoI at 37° C. for 1 hour. This treatment produces two DNA fragments of 6.2 kb and 1.0 kb, respectively. The two fragments were separated by agarose gel electrophoresis and were purified using β-agarose (Biolabs), as recommended by the supplier.

At the same time, 1 μg of the plasmid pBCKS was cut with the restriction endonucleases XhoI and HindIII for 1 hour at 37° C. and they were heated at 65° C. for 10 minutes in order to stop the reaction.

The sample containing the purified DNA fragment of 1.0 kb was mixed with the pBCKS plasmid digestion sample and they were ligated using the DNA-ligase enzyme of the phage T4.

An aliquot of the ligation mixture was used to transform competent Escherichia coli TG1 bacteria. The strains containing recombinant plasmids were isolated by growing them in a solid culture medium containing LB, chloramphenicol (34 μg/ml), 5-bromo-4-chloro-indolyl-b-D-galactoside (X-Gal) (40 μg/ml) and isopropylthio-b-D-galactoside (IPTG) (0.2 mM). The strains with recombinant plasmids were distinguished in this medium by the fact that they produce white colonies, as compared with the blue colonies produced by the non-recombinant strains. In this way it was possible to isolate one of the recombinant clones possessed by the plasmid pJCE20, the map of which is shown in the drawing.

An aliquot of the plasmid pJCE20 (2 μg) was then digested with the restriction endonucleases KpnI and HindIII for 1 hour at 37° C. The resultant 1.0-kb fragment was purified in the same way as before, using β-agarose. At the same time, 0.3 μg of double-stranded DNA from M13tg131 was digested with the same enzymes for 1 hour at 37° C. and inactivated by heating the sample at 65° C. for 10 minutes. The purified 1.0-kb KpnI-HindIII fragment and the digested M13tg131 were ligated in the presence of T4 DNA-ligase for 16 hours at 16° C. An aliquot of the ligation mixture was used to transform competent Escherichia coli TG1 and the recombinant phages were selected on LB plates in the presence of X-Gal and IPTG. The white lysis plaques correspond to phages with an insert. One of these recombinant phages, called M13Glu7, which contained the fragment of the gla gene, was used to prepare the single DNA strand needed to perform the site-directed mutagenesis. This mutagenesis was carried out using the site-directed mutagenesis kit supplied by Amersham and the 33-mer synthetic oligo-nucleotide (5'-GCGCTGGCCGAGCCCGGGCTCGACGCCGCAGGC-3') (SEQ ID NO:1), in accordance with the suppliers' instructions.

In this way it was possible to obtain the phage M13GSM7 which contained the DNA fragment corresponding to a part of the gla gene with a new SmaI restriction target.

2. Subcloning of the Modified Fragment in Order to Reconstruct the gla Gene with an SmaI Target.

The replicative form of the recombinant phage M13GSM7 containing the SmaI restriction site, obtained as described in the preceding section, was digested with the restriction endonucleases HindIII and HhoI at 37° C. for 1 hour. The 1.0-kb fragment produced by this digestion was purified using β-agarase and ligated with the 6.5-Kb fragment of pJC200 previously purified in the presence of the T4 DNA-ligase. The ligation mixture was used to transform competent Escherichia coli TG1 cells. The plasmids of the recombinant clones were analysed on the basis of their size and restriction map and in this way it was possible to isolate the plasmid pJCSM72 which contains the modified gla gene with an additional nucleotide in position 93 which prevents the expression of the gla gene. For this reason the recombinant Escherichia coli TG1 clone (pJCSM72) does not produce GLA activity.

The plasmid pJCSM72 contains a target for the restriction endonuclease NK SmaI which allows the insertion in this position of a small DNA fragment, called HIS1.2, which codes for six histidines and which is obtained by mixing two synthetic oligonucleotides (5'CATCATCACCACCATCACTT-3' (SEQ ID NO:2) and 3'-GTAGTAGTGGTGGTAGTGAA-5') (SEQ ID NO:3).

The plasmid pJCSM72 was cut with the restriction enzyme SmaI at 25° C. for 3–4 hours and the enzyme was inactivated at 65° C. for 10 min. An aliquot of the digest (0.3 μg) was ligated with 1.2 μg of the fragment HIS1.2 in the presence of T4 DNA-ligase. In order to select the recombinant clones which contain a plasmid with the fragment HIS1.2 inserted in the right direction, competent Escherichia coli HB101 cells were transformed with the ligation mixture and selected in a medium containing glutaryl-L-leucine as the sole source of L-leucine. In this way only the recombinant clones which contain a plasmid with the fragment HIS1.2 inserted in the right direction, and which therefore produce active GLA, will be able to grow in this medium. In order to perform this selection, the transformed cells were sedimented and washed with a solution of NaCl (8.5 g/l), and they were then inoculated in a minimal medium made up of M9 saline medium ($Na_2HPO_4$ (6 g/l), $KH_2PO_4$ (3 g/l), NaCl (0.5 g/l), $NH_4Cl$ (1 g/l), glucose (2 g/l), thiamine-HCl (1 mg/l), L-proline (100 mg/l), chloramphenicol (50 mg/l) and glutaryl-L-leucine (100 mg/l)). The plates were incubated at 30° C., and after 5 days clones containing the recombinant plasmid pHG6 were obtained (see drawing). The presence of a sequence coding for the six histidines in the plasmid pHG6 was confirmed by DNA sequencing.

In order to determine whether the Escherichia coli CECT 4637 cells produced GLA, they were grown for 48 hours at 30° C. in 1 liter of LB medium containing chloramphenicol (34 mg/l). The culture was centrifuged at 14,000×g for 10 min, and the sedimented cells were resuspended in 30 ml of 10 mM sodium phosphate buffer (pH 7.0) and disrupted by sonication. The extract was cooled to 4° C. and centrifuged at 30,000×g for 30 min. The GLA activity was assayed in the supernatant and it was found that this activity was comparable to that obtained with Escherichia coli extracts (pJC200), suggesting that the modification produced in the GLA by the insertion of the six histidines does not radically affect the activity of the enzyme.

EXAMPLE 3
1. Production of Modified GLA with the Chain of Histidines

The *Escherichia coli* CECT 4637 cells were grown for 48 hours at 30° C. in 1 liter of LB medium containing chloramphenicol (34 mg/l). The culture was centrifuged at 14,000×g for 10 min, and the sedimented cells were resuspended in 30 ml of 10 mM sodium phosphate buffer (pH 7.0) containing 0.2 M NaCl and 7 mM imidazole and were disrupted by sonication. From this point onwards, all the steps were carried out at 4° C. The enzyme extract was applied to an IDA-Cu 6BCL chelate column (1.2×1.76 cm), equilibrated with 10 mM sodium phosphate buffer (pH 7.0), 0.2 M NaCl and 7 mM imidazole. The elution flow of the column was controlled with a Bio-Rad Econo-System at 0.5 ml/min. The column was washed first with 5 volumes of the same buffer and then with 5 volumes of a further two buffers, similar to the preceding one but containing 15 mM and 30 mM imidazole, respectively.

The GLA activity of each fraction was assayed as detailed in Table 1. The proteins present in each fraction were observed by SDS polyacrylamide gel electrophoresis.

TABLE 1

Purification of the glutaryl 7 ACA expressed by *Escherichia coli* CECT 4637

| FRACTION | TOTAL ACTIVITY nmoles/min | YIELD % | SPECIFIC ACTIVITY nmoles/min × mg |
|---|---|---|---|
| Load | 1792 | 100 | 58 |
| Load eluate | 246 | 14 | 9 |
| 7 mM Imidazole | 76 | 4 | 41 |
| 15 mM Imidazole | 316 | 18 | 518 |
| 30 mM Imidazole | 810 | 48 | 6750 |

The greatest GLA activity (approximately 50% of the total activity loaded onto the column) is concentrated in the fraction eluted with 30 mM imidazole, and the GLA enzyme is obtained virtually pure. SDS polyacrylamide gel electrophoresis showed that the purified GLA enzyme has two polypeptides of 16,000 and 54,000 Da which represent the two chains of the protein.

In order to demonstrate the presence of contaminant esterases, the ability of each fraction of the purification process to hydrolyse p-nitrophenyl-acetate (PNA) was measured. Prior to the assay it is necessary to dialyse each fraction of the purification process in order to eliminate the imidazole contained therein, as this compound spontaneously hydrolyses p-nitrophenol esters.

As is shown in Table 2, the fraction eluted with 30 mM imidazole, which contains the pure Gla enzyme, does not exhibit any esterase activity on the substrate PNA, compared with the extract before purification. For this reason, the purification of modified GLA with a chain of polyhistidines, expressed by the strain *Escherichia coli* CECT 4637, avoids the co-purification of esterases which can reduce the yield from the industrial process for obtaining 7ACA.

TABLE 2

Esterase activity of the fractions isolated during the process of purification of glutaryl 7ACA acylase expressed by *Escherichia coli* CECT 4637.

| FRACTION | TOTAL ACTIVITY nmoles/min |
|---|---|
| Load | 360 |
| Load eluate | 134 |
| 7 mM Imidazole | 34 |
| 15 mM Imidazole | 7 |
| 30 mM Imidazole | 0 |

The drawing shows a representation of the genetic constructs created for obtaining the plasmid pHG6. The plasmids and M13 phages are represented in circles.

Abbreviations: H, HindIII; K, KpnI; X, XbaI; cam, chloramphenicol acetyltransferase gene; tac$^P$, tac promoter.

---

What is claimed is:

1. A procedure for modifying a native 7β-(4-carboxybutanamide) cephalosporinase enzyme to produce a modified 7β-(4-carboxybutanamide) cephalosporinase enzyme in host cells, said native enzyme having alpha and beta subunits, said method comprising the steps of:
   (a) conducting site directed mutagenesis in a gene encoding said native 7β-(4-carboxybutanamide) cephalosporinase enzyme by inserting in the gene a nucleotide sequence encoding a chain of at least six histidines at a site in the gene encoding the N-terminal region of the alpha subunit that is 3' to a sequence coding for Leu-Ala-Glu-Pro such that (i) the modified enzyme with the chain of at least six histidines has an activity and enzymatic specificity which are not significantly changed from that of the native enzyme, and (ii) the chain of at least six histidines is present in an area of the modified enzyme in which it can interact with a metal chelate on a chromatographic support;
   (b) fusing said mutagenized gene with a promoter for the expression of mutagenized gene to form a fusion gene construct;
   (c) transforming host cells with the fusion gene construct;
   (d) growing the transformed host cells in a suitable culture medium and under conditions allowing expression of the modified 7β-(4-carboxybutanamide) cephalosporinase enzyme comprising the chain of at least six histidines; and
   (e) recovering the modified 7β-(4-carboxybutanamide) cephalosporinase enzyme with the chain of at least six histidines from the culture medium by a process comprising centrifuging to separate the transformed cells from the culture medium, disrupting the transformed host cells to form a cell extract and purifying the cell extract by chromatography on a chromatographic support containing a metal chelate.

2. A procedure as claimed in claim 1, wherein the fusion gene construct comprises a chloramphenicol resistance gene as a selectable marker.

3. A procedure according to claim 1, wherein the transformed host cells are grown for 48 hours at 30° C. in LB medium.

4. A procedure according to claim 1, wherein the host cells are of *Escherichia coli*.

5. A procedure according to claim 1, wherein the gene sequence subjected to mutation is obtained from Acinetobacter sp. ATCC 53891.

6. A procedure according to claim 4, wherein the gene sequence is the gla gene.

7. 7β-(4-Carboxybutanamide) cephalosporinacylase enzyme obtained by the procedure of claim 1.

8. An isolated DNA encoding a 7β-(4-carboxybutanamide) cephalosporinase enzyme with an N-terminal region having a tetrapeptide consisting of Leu-Ala-Glu-Pro, said enzyme comprising a sequence of at least six histidines at a site carboxyl-proximal to the tetrapeptide in the N-terminal region of the enzyme.

9. An isolated DNA according to claim 8, wherein the enzyme comprises the amino acid sequence of SEQ ID NO:8.

10. An isolated DNA according to claim 9 comprising SEQ ID NO:7.

11. An isolated DNA encoding the amino acid sequence of SEQ ID NO: 8.

12. An isolated DNA according to claim 11, comprising SEQ ID NO:7.

13. A vector comprising the isolated DNA of claim 10.

14. Plasmid pHG6.

15. Host cells selected from the group consisting of a pure culture of *Escherichia coli* CECT 4637, mutants thereof and transformed derivatives thereof.

16. A method for recovering modified 7β-(4-carboxybutanamide) cephalosporinacylase comprising disrupting the host cells of claim 11 to obtain a cell extract and purifying the cell extract by chromatography on a chromatographic support containing a metal chelate.

17. A modified cephalosporinacylase recovered by the method of claim 16.

18. In a method of synthesizing 7-aminocephalosporanic acid from 7β-(4-carboxybutanamide) cephalosporanic acid with the aid of an enzyme with cephalosprinacylase activity, the improvement comprising catalyzing the synthesis with the cephalosporinascylase enzyme of claim 7.

* * * * *

UNITED STATES PATENT AND TRADEMARK OFFICE
CERTIFICATE OF CORRECTION

PATENT NO. : 6,146,871
DATED : November 14, 2000
INVENTOR(S) : Jose Luis Garcia Lopez, et al.

It is certified that error appears in the above-identified patent and that said Letters Patent is hereby corrected as shown below:

On title page, item 73, "Sntibioticos" should read -- Antibioticos --.

Signed and Sealed this

Eighth Day of May, 2001

*Attest:*

NICHOLAS P. GODICI

*Attesting Officer*     *Acting Director of the United States Patent and Trademark Office*

SEQUENCE LISTING

<160> NUMBER OF SEQ ID NOS: 8

<210> SEQ ID NO 1
<211> LENGTH: 33
<212> TYPE: DNA
<213> ORGANISM: Artificial Sequence
<220> FEATURE:
<223> OTHER INFORMATION: Synthetic oligonucleotide for site-directed
      mutagenesis of gla gene

<400> SEQUENCE: 1
gcgctggccg agcccgggct cgacgccgca ggc                              33

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide encoding six
      histidines

<400> SEQUENCE: 2

```
catcatcacc accatcactt                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide that is
      complementary to the synthetic oligonucleotide encoding six
      histidines

<400> SEQUENCE: 3
gtagtagtgg tggtagtgaa                                              20

<210> SEQ ID NO 4
<211> LENGTH: 18
<212> TYPE: DNA
<213> ORGANISM: Acinetobacter sp.

<400> SEQUENCE: 4
ctggccgagc cgacctcg                                                18

<210> SEQ ID NO 5
<211> LENGTH: 16
<212> TYPE: DNA
<213> ORGANISM: Artificial Sequence
<220> FEATURE:
<223> OTHER INFORMATION: Synthetic oligonucleotide for site-directed
      mutagenesis of gla gene

<400> SEQUENCE: 5
gccgagcccg ggctcg                                                  16

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide from gla gene
      modified to include a Sma. I restriction site
<220> FEATURE:
<223> OTHER INFORMATION: Gla gene modified to encode six histidines

<400> SEQUENCE: 6
ctggccgagc ccgggctdg                                               19

<210> SEQ ID NO 7
<211> LENGTH: 39
<212> TYPE: DNA
<213> ORGANISM: Artificial Sequence
<220> FEATURE:
<223> OTHER INFORMATION: Gla gene modified to encode six histidines

<400> SEQUENCE: 7
ctggccgagc cccatcatca ccaccatcac ttgggctcg                         39

<210> SEQ ID NO 8
<211> LENGTH: 13
<212> TYPE: PRT
<213> ORGANISM: Artificial Sequence
```

```
-continued

<220> FEATURE:
<223> OTHER INFORMATION: Gla peptide modified to include six histidines

<400> SEQUENCE: 8

Leu Ala Gln Pro His His His His His His Leu Gly Ser
 1               5                  10
```